United States Patent
Jarrell

(10) Patent No.: US 10,668,259 B2
(45) Date of Patent: Jun. 2, 2020

(54) METAL OXIDE AND POLYMER CONTROLLED DELIVERY SYSTEMS, SUNSCREENS, TREATMENTS, AND TOPICAL COATING APPLICATORS

(71) Applicant: John D. Jarrell, East Greenwich, RI (US)

(72) Inventor: John D. Jarrell, East Greenwich, RI (US)

(73) Assignee: Materials Science Associates, LLC, Coventry, RI (US)

( * ) Notice: Subject to any disclaimer, the term of this patent is extended or adjusted under 35 U.S.C. 154(b) by 404 days.

(21) Appl. No.: 15/331,063

(22) Filed: Oct. 21, 2016

(65) Prior Publication Data

US 2017/0165462 A1 Jun. 15, 2017

Related U.S. Application Data

(60) Provisional application No. 62/244,706, filed on Oct. 21, 2015.

(51) Int. Cl.
*A61M 35/00* (2006.01)
*A61K 9/00* (2006.01)
(Continued)

(52) U.S. Cl.
CPC ............. *A61M 35/003* (2013.01); *A61K 8/27* (2013.01); *A61K 8/29* (2013.01); *A61K 8/35* (2013.01); *A61K 8/37* (2013.01); *A61K 8/40* (2013.01); *A61K 8/411* (2013.01); *A61K 8/445* (2013.01); *A61K 8/466* (2013.01); *A61K 8/4946* (2013.01); *A61K 8/898* (2013.01); *A61K 9/0014* (2013.01); *A61K 31/138* (2013.01); *A61K 31/192* (2013.01); *A61K 31/4545* (2013.01); *A61K 47/02* (2013.01); *A61K 47/06* (2013.01); *A61K 47/10* (2013.01); *A61K 47/34* (2013.01); *A61Q 17/04* (2013.01); *A61K 2800/872* (2013.01);
(Continued)

(58) Field of Classification Search
CPC ......... A61M 35/003; A61K 8/27; A61K 8/29; A61K 8/35; A61K 8/37; A61K 8/40; A61K 8/411; A61K 8/445; A61K 8/466; A61K 8/4946; A61K 8/898
USPC ................................................. 424/409–449
See application file for complete search history.

(56) References Cited

U.S. PATENT DOCUMENTS

| 4,593,836 A | 6/1986 | Lilienthal |
| 5,084,365 A | 1/1992 | Gratzel et al. |

(Continued)

OTHER PUBLICATIONS

European Search Report for European Patent Application No. 08838814.5, dated Mar. 14, 2014, 7 pages.
(Continued)

*Primary Examiner* — Tatyana Zalukaeva
*Assistant Examiner* — Gabriella E Burnette
(74) *Attorney, Agent, or Firm* — Adler Pollock & Sheehan P.C

(57) ABSTRACT

Systems and methods for keeping various compounds stable in different ampoules in an applicator. Upon breaking open the ampoules, the compounds are mixed and applied. In one embodiment, the resulting mixture is a long lasting waterproof sunscreen for use on skin. In another embodiment, the resulting mixture applied one or more coatings to an article and may subsequently accomplish sustained release and/or transdermal deliver of a therapeutic.

14 Claims, 6 Drawing Sheets

(51) Int. Cl.
| | |
|---|---|
| *A61K 47/06* | (2006.01) |
| *A61K 47/34* | (2017.01) |
| *A61K 31/4545* | (2006.01) |
| *A61K 31/138* | (2006.01) |
| *A61Q 17/04* | (2006.01) |
| *A61K 8/46* | (2006.01) |
| *A61K 8/29* | (2006.01) |
| *A61K 8/27* | (2006.01) |
| *A61K 47/02* | (2006.01) |
| *A61K 47/10* | (2017.01) |
| *A61K 31/192* | (2006.01) |
| *A61K 8/35* | (2006.01) |
| *A61K 8/37* | (2006.01) |
| *A61K 8/41* | (2006.01) |
| *A61K 8/40* | (2006.01) |
| *A61K 8/49* | (2006.01) |
| *A61K 8/898* | (2006.01) |
| *A61K 8/44* | (2006.01) |
| *A61K 8/11* | (2006.01) |

(52) U.S. Cl.
CPC .... *A61K 2800/882* (2013.01); *A61K 2800/95* (2013.01)

(56) References Cited

U.S. PATENT DOCUMENTS

| | | | |
|---|---|---|---|
| 5,489,304 | A | 2/1996 | Orgill et al. |
| 6,013,372 | A | 1/2000 | Hayakawa et al. |
| 6,066,581 | A | 5/2000 | Chivukula et al. |
| 6,403,689 | B1 | 6/2002 | Lehaut et al. |
| 6,548,590 | B1 | 4/2003 | Koloski et al. |
| 6,599,631 | B2 | 7/2003 | Kambe et al. |
| 6,743,517 | B2 | 6/2004 | Nakamura et al. |
| 6,810,288 | B2 | 10/2004 | Joshi |
| 7,014,799 | B2 | 3/2006 | Yang et al. |
| 7,118,727 | B2 | 10/2006 | Williams |
| 7,153,357 | B2 | 12/2006 | Baumgart et al. |
| 7,175,611 | B2 | 2/2007 | Mitchnick |
| 7,176,245 | B2 | 2/2007 | Stucky et al. |
| 7,223,378 | B2 | 5/2007 | Sterzel |
| 7,226,966 | B2 | 6/2007 | Kambe et al. |
| 7,789,278 | B2 | 9/2010 | Ruiz de Gopegui et al. |
| 7,868,078 | B2 | 1/2011 | Jarrell |
| 7,906,132 | B2 | 3/2011 | Ziegler et al. |
| 8,080,223 | B2 | 12/2011 | Jarrell et al. |
| 2002/0192196 | A1 | 12/2002 | Allen-Hoffmann |
| 2003/0031438 | A1 | 2/2003 | Kambe et al. |
| 2003/0091542 | A1 | 5/2003 | Eberhardt et al. |
| 2003/0116273 | A1 | 6/2003 | Nakamura et al. |
| 2003/0157248 | A1 | 8/2003 | Watkins et al. |
| 2003/0229319 | A1 | 12/2003 | Mitchnick |
| 2003/0235653 | A1 | 12/2003 | Yu |
| 2004/0115239 | A1 | 6/2004 | Shastri et al. |
| 2004/0129112 | A1 | 7/2004 | Gillis et al. |
| 2004/0161473 | A1 | 8/2004 | Joshi |
| 2005/0170192 | A1 | 8/2005 | Kambe et al. |
| 2006/0013982 | A1 | 1/2006 | Malik et al. |
| 2006/0161256 | A1 | 7/2006 | Ziegler et al. |
| 2007/0071879 | A1 | 3/2007 | Rypacek et al. |
| 2007/0196663 | A1 | 8/2007 | Schwartz et al. |
| 2007/0202342 | A1 | 8/2007 | Whiteford et al. |
| 2007/0224116 | A1 | 9/2007 | Chandrasekaran et al. |
| 2008/0004390 | A1 | 1/2008 | Aoshima et al. |
| 2009/0050852 | A1 | 2/2009 | Kanamori et al. |
| 2009/0104095 | A1* | 4/2009 | Morgan .............. C01G 1/02 423/23 |
| 2009/0104473 | A1 | 4/2009 | Morgan et al. |
| 2009/0105384 | A1 | 4/2009 | Morgan et al. |
| 2009/0317624 | A1 | 12/2009 | Yoshioka et al. |
| 2010/0183829 | A1 | 7/2010 | Jarvekulg et al. |
| 2011/0092870 | A1 | 4/2011 | Jarrell |
| 2015/0306362 | A1* | 10/2015 | Battaglia .............. A61M 35/006 206/364 |

OTHER PUBLICATIONS

Yabua Takeshi, Tsuru Kanji, Hayakawa Satoshi, Osaka Akiyoshi, "Synthesis of Blood Compatible PDMS-Based Organic-Inorganic Hybrid Coatings", Journal of Sol-Gel Science and Technology, 31, 273-276, Kluwer Academic Publishers, 2004.

Iketani Kazuya, Sun Ren-De, Toki Motoyuki, Hirota Ken, Yamaguchi Osamu, "Sol-gel-derived TiO2/poly (dimethylsiloxane) hybrid films and their photocatalytic activities", Journal of Physics and Chemistry of Solids, 64 (2003) 507-513, Elsevier Science Ltd.

Nakade Masato, Kameyama Koichi, Ogawa Makoto, "Synthesis and properties of titanium dioxide/polydimethylsiloxane hybrid particles", Journal of Material Science, 39 (2004) 4131-4137, Kluwer Academic Publishers 2004.

Anpo, Masakazu, "Preparation, Characterization, and Reactivities of Highly Functional Titanium Oxide-Based Photocataiysts Able to Operate under UV-Visible Light Irradiation: Approaches in Realizing High Efficiency in the Use of Visible Light", Bull. Chem. Soc. Jpn., 77, 1427-1442 (2004).

Lin Yu-Ting, Zeng Tsung-Wei, Lai Wei-Zong, Chen Chun-Wei, Lin Yun-Yue, Chang Yu-Sheng, Su Wei-Fang, "Efficient photoinduced charge transfer in TiO2 nanorod/conjugated polymer hybrid materials", Nanotechnology 17 (2006) 5781-5785, Institute of Physics Publishing LTD, Printed in UK.

Kroon J.M., Veenstra S.C., Sloof L.H., Verhees W.J.H., Koetse M.M., Sweelssen J., Schoo H.F.M., Beek W.J.E., Wienk M.M., Janssen R.A.J., Yang X., Loos J., Michailetchi V.D., Blom P.W.M., Knol J., Hummelen J.C., "Polymer Based Photovoltaics: Novel Concepts, Materials and State-of-the-Art Efficiencies", Presented at the 20th European Photovoltaic Solar Energy Conference and exhibition, Barcelona, Spain, Jun. 6-10, 2005.

Tada Hiroaki, Mitsui Tomohiro, Kiyonaga Tomokazu, Akita Tomoki, Tanaka Koji, "All-Solid-State Z-scheme in CdS—Au—TiO2 three-component nanojunction system", Nature Publishing Group 5, 782-786. Oct. 2006.

Alonso Bruno, Maquet Jocelyne, Viana Bruno, Sanchez Clement, "Hybrid organic-inorganic polydimethylsiloxane-vanadium-oxo materials crosslinked at the molecular level", New J. Chem., 1996, pp. 935-939.

Jarrell John D.,"Metal Oxide Coated (MOC) Cell Culture Arrays for Rapid Biological Screening", Graduate Program in Biomedical Engineering, Brown University, Providence, RI, Aug. 15, 2006.

Luo, X. et al., Journal of Sol-Gel Science and Technology, vol. 321, p. 297-301, 2004.

Fujishima, A. et al., Journal of Photochemistry and Photobiology C: Photochemistry Reviews, vol. 1, p. 1-21, 2000.

Jarrell, John D. (May 2008), Active metal oxides and polymer hybrids as biomaterials (Doctoral Dissertation). Retrieved from Proquest Dissertations and Theses Database, (UMI 3335664).

Park et al (Editors), "Mesostructured TiO2 films as effective photocatalysts for the degradation of organic pollutants", Studies in Surface Science and Catalysis (2003), 146 (Nanotechnology in Mesostructured Matierals), 601-604.

Jarrell, J.D., Eun, T.H., Samale, M., Briant, C., Sheldon, B.W., Morgan, J.W. "Metal oxide coated cell culture arrays for rapid biological screening." Journal of Biomedical Materials Research Part A; vol. 83A, p. 853-860.

Dow Corning Toray PRX 413 Fluid Material Safety Data Sheet, 2008, 6 pages.

* cited by examiner

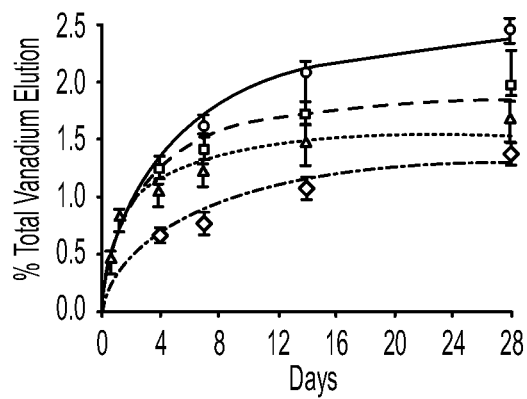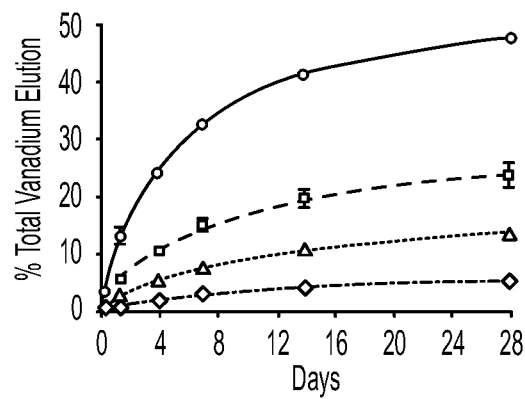
FIG. 1A  FIG. 1B
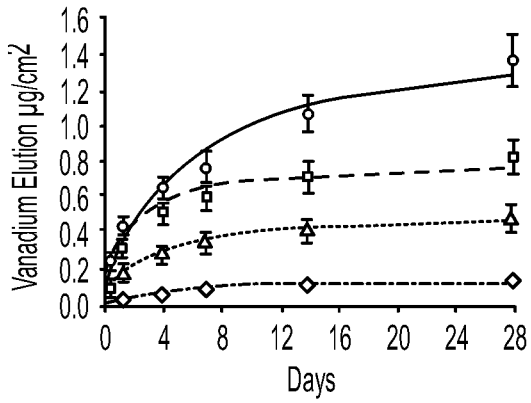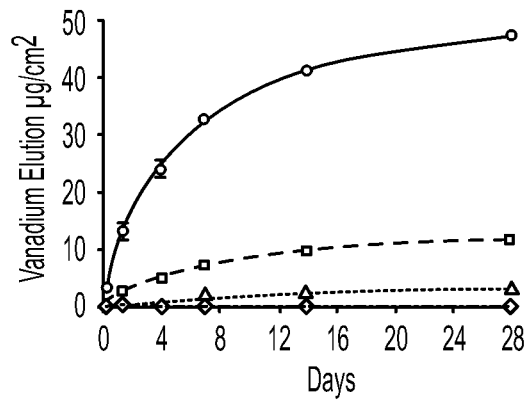
FIG. 1C  FIG. 1D

METAL OXIDE AND POLYMER CONTROLLED DELIVERY SYSTEMS, SUNSCREENS, TREATMENTS, AND TOPICAL COATING APPLICATORS

CROSS-REFERENCE TO RELATED APPLICATION

This application claims priority to U.S. Provisional Patent Application No. 62/244,706, filed Oct. 21, 2015, which is incorporated herein by reference.

FIELD OF THE INVENTION

The subject disclosure relates to compositions, as well as related methods, coatings, and delivery mechanisms.

BACKGROUND OF THE INVENTION

The greatest obstacle for transdermal drug delivery is the stratum corneum that forms a primary rate limiting barrier to the permeation of drugs across the skin. It consists of dead, flattened cells filled with keratin that are embedded in a lipid matrix. The stratum corneum has been described as hydrophilic protein bricks embedded in a hydrophobic lipid mortar. There has been a considerable interest in the potential usefulness of the topical application of non-steroidal anti-inflammatory drugs (NSAIDs) such as ibuprofen, indomethacin and diclofenac. These weak acidic drugs are effective in the treatment of rheumatoid arthritis and osteoarthritis.

However, the disadvantage of the topical route for drug delivery is that a relatively high dose is required to deliver therapeutic amounts of drug across the skin. To improve the topical delivery of drugs, several strategies are available including the use of penetration enhancers and optimization of drug release from the formulation. The pH of the formulation has an impact on the penetration rate of weak acidic and weak basic drugs.

The flux of ibuprofen from a saturated solution at pH values ranging from 2.2 to 9.0 using human skin in vitro has been studied. It was reported that flux of the drug increased with an increase in the pH of the solution. The reason behind this effect was unclear. However, ibuprofen was reported to show a considerable surface activity. Since surfactants are well known penetration enhancers, it is possible that ibuprofen has acted as surfactant and thus impaired the skin permeability barrier. Hence, it is planned to study effect of ibuprofen concentration, in saturated solutions, on its permeation across skin. It is a known concept that an increase in concentration of drug in the vehicle results in enhanced flux due to increased thermodynamic activity. One delivery mechanism was designed by keeping thermodynamic activity constant while increasing the drug concentration in the delivery mechanism. This was done by preparing saturated solutions of ibuprofen, of different concentrations, using disodium hydrogen phosphate solutions of various molar strengths. The permeation of ibuprofen from its saturated solutions across rat epidermis and human epidermis was studied, and the results were compared with those obtained from silastic membrane.

The transdermal route now ranks with oral treatment as the most successful innovative research area in drug delivery, with around 40% of the drug delivery candidate products under clinical evaluation related to transdermal or dermal system. The worldwide transdermal patch market approaches £ 2 billion, based on only ten drugs including scopolamine, nitroglycerine, clonidine, estrogen, testosterone, fentanyl, and nicotine, with a lidocaine patch soon to be marketed.

SUMMARY

The success of a dermatological drug to be used for systemic drug delivery depends on the ability of the drug to penetrate through skin in sufficient quantities to achieve the desired therapeutic effect. The subject technology uses chemical penetration enhancers and the associated possible mechanisms of action.

Reservoir and barrier systems are commonly used for controlled release in applications such as transdermal drug delivery and with implantable systems of similar design. The drug or active ingredient is often in a liquid or gel state and is delivered across a rate controlling polymer membrane. These systems have the advantage of providing near zero order release characteristics. This means that such a system delivers a consistent amount of drug or active ingredient over an extended period of time. One disadvantage of such systems is the sudden and uncontrolled release of drug or active ingredient if the barrier is disrupted or a defect is present in the barrier or rate controlling membrane. To reduce the occurrence of leakage resulting in the uncontrolled release of drugs or active ingredients, some delivery systems use a solid matrix delivery system. This consists of a polymer or mixture of copolymers, drugs or active ingredients with or without a rate controlling membrane and often agents designed to improve release and skin permeation properties.

Metal oxide based delivery systems have been described in a past patents (U.S. Pat. No. 7,906,132, Anti-infectious, biocompatible titanium coating for implants, and method for the production thereof to Ziegler et al. issued on Mar. 15, 2011) and published in the literature (Jarrell J D, Dolly B, Morgan J R. Controlled release of vanadium from titanium oxide coatings for improved integration of soft tissue implants. J Biomed Mater Res A, Volume 90A, Issue 1, Pages 272-281, June 2009). In these cases, the drugs or active ingredients are distributed within a matrix of metal oxides and applied in the form of coatings or bulk materials. One drawback of these systems is that it is difficult to deliver much of the drug or active ingredient loaded into the matrix. These dopants become trapped within the matrix.

In the case where refractory and transitional metal oxide matrices consisting of titanium, zirconium, niobium and or tantalum oxides are doped with water soluble metals or metal oxides of silver, vanadium, zinc and or copper and similar agents to provide bioactive and antimicrobial activity, much of the doped ingredients become trapped within the matrix. This was demonstrated in a publication by Jarrell et al. (Jarrell J D, Dolly B, Morgan J R. Rapid screening, in vitro study of metal oxide and polymer hybrids as delivery coatings for improved soft-tissue integration of implants. J Biomed Mater Res A, Volume 92A, Issue 3, Pages 1094-1104, 1 Mar. 2010). In these experiments coatings of pure titanium oxide matrices doped with vanadium oxide, released vanadium at a much lower rate than similarly doped titanium oxide and polymer hybridized matrix coatings.

In a liquid formula, a bather includes a polymer or metal oxide. In a suntan lotion formula, the liquid compositions are sunscreen precursors, where metal oxide can be added (not using two layers). Preferably, the suntan lotion is organic and can be sprayed on from a can. For drug delivery, a layer makes a reservoir coating—made from silver plus a polymer—with or without diffusion layers. It can be 2 separate layers, either layer or both of a reservoir and barrier layer. There can also be 2 applicator with one or more layers in each applicator. Either of which can form film of the bather coating. It should be appreciated that the subject technology can be implemented and utilized in numerous ways, including without limitation as a process, an apparatus, a system, a device, a method for applications now known and later developed. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the drawings.

FIG. 1A illustrates a plot (a) in accordance with the subject technology.

FIG. 1B illustrates a plot (b) in accordance with the subject technology.

FIG. 1C illustrates a plot (c) in accordance with the subject technology.

FIG. 1D illustrates a plot (d) in accordance with the subject technology.

DESCRIPTION OF PREFERRED EMBODIMENTS

Figure 2:
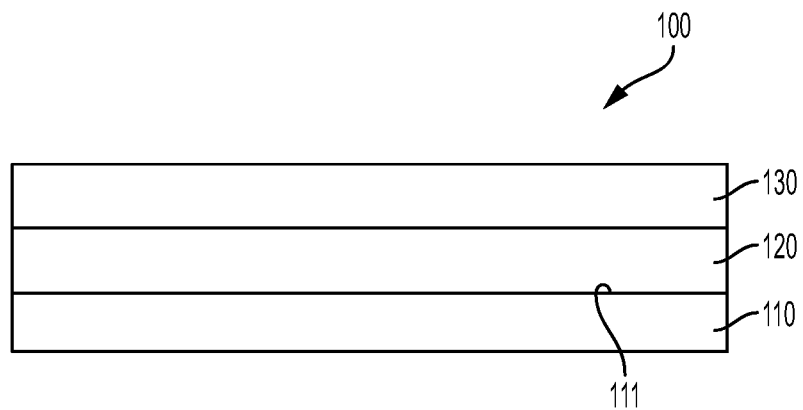
FIG. 2 is a cross-sectional view of a coated article in accordance with the subject technology.

The advantages, and other features of the technology disclosed herein, will become more readily apparent to those having ordinary skill in the art from the following detailed description of certain preferred embodiments taken in conjunction with the drawings which set forth representative embodiments of the present technology.

Referring to FIGS. 1A-1D, four plots (a)-(d) are shown. The top plots (a), (b) illustrate how addition of Polydimethylsiloxane (PDMS) to titanium coatings increases the elution rate of vanadium. Plots (a), (b) present the percentage of total vanadium loading released into PBS as a function of time for titanium oxide coatings without PDMS (left, open symbols) and 66.6% Titanium oxide—33.4% PDMS hybrid coatings (right, closed symbols), while the lower plots (c), (d) are the cumulative release rates per surface area over the same period for four different vanadium concentrations, 20% (circles), 10% (squares), 5% (triangles) and 1.25% (diamonds). Modeling curves of vanadium release are shown for 20% (----) 10% (---) 5% (· · · ·) and 1.25% (-· ·-·-·) vanadium doping. As can be seen, titanium oxide doped with 20% vanadium oxide released approximately 2.5% of the total vanadium loading after 28 days. However, 66.6% Titanium oxide and 33.4% Polydimethylsiloxane hybrid coatings doped with the same amount of vanadium oxide (20%), released approximately 50% of the total vanadium loading after 28 days. The result being that polymer hybridization of the metal oxides improved the rate of delivery of dopants.

One factor which limits the use of coatings as a delivery matrix is the total volume available for drug loading. The limit is constrained by the thickness and area of the coatings. This is compounded by the fact that the metal oxides and polymers selected for the matrix (i.e. titanium oxide, tantalum oxide, zirconium oxide, niobium oxide) are generally used to both improve the biocompatibility of the surface coating with surrounding tissues and cells and control the rate of delivery of the doped agent. If excessive levels of doping are used in the matrix (for example, over 50% Ag or V) then the properties of the matrix materials are increasingly lost, delivery rates may become excessively high and outside of the therapeutic range and sustained release can be compromised and prevented.

To overcome these problems and further enhance and prolong the delivery from metal oxide and polymer hybrid coating systems, multiple layers of coatings may be used. These can be multiple layers of the same coatings. However there is a limitation to number and thickness of coatings that can be used without compromising the mechanical properties and aesthetic appearance of the coatings.

To overcome the limitations of multiple coatings of the same composition, the subject technology includes a multi-layer coating system, where the innermost layer or layers contain a higher concentration of the active ingredient or ingredients and act as a reservoir, while the outer layer or layers contain lower concentrations of the active ingredient or ingredients and act as a rate controlling diffusion barrier.

When exposed to liquids or bodily fluids, the liquid diffuses through the barrier coating and releases the active ingredient into the surrounding liquids or bodily tissues. The active ingredients in the reservoir layer move down the diffusion gradient and replace the ions or active ingredients lost within the barrier layer, thus provided sustained and prolonged release over the single or multiple coatings without the reservoir layer design. This way the biocompatible and rate limiting properties of the barrier layer or layers are also maintained. Put in other terms, the outermost coating acts as a diffusion barrier, while the underlying coatings can function as solid state, gel, sol or xerogel reservoir containing higher concentrations of the active agents for elution or controlled delivery through the rate controlling diffusion barrier. This is an improvement upon existing systems using single or multiple coatings containing the same or similar levels of the active ingredient for elution. This has the advantage of providing a reservoir for allowing for longer, sustained release through the coatings systems. The use of a rate controlling barrier film also prevents excessively high release of the active ingredient when such can have negative therapeutic results. This allows the diffusion barrier to have lower levels of delivered agents and be optimized for tissue contact, cellular adhesion, cell proliferation, inflammatory properties and biocompatibility, since it is no longer the primary reservoir for the delivered agent.

Referring now to FIG. 2, a cross-sectional view of a coated article 100 is shown. The coated article 100 includes an object 110 and a reservoir coating 120 supported on a surface 111 of object 110 and a diffusion barrier coating 130. In general, upper coating 130 includes a metal oxide and a polymer, while lower coating 120 includes a higher level of active ingredients for delivery with or without additional matrix forming metal oxides and polymers. The metals and metal oxides that can be used in coating 120 generally include those which exhibit one or more therapeutic effects under a certain condition. In some embodiments, the metal oxide in coating 120 is a transition metal oxide. Examples of suitable metal oxides for use in coating 120 include titanium oxides, vanadium oxides, zinc oxides, zirconium oxides, silver oxides, tantalum oxides, or combinations thereof. In other embodiments coating 120 consists of a drug, biologic, peptide, protein, glycoprotein, polysaccharide, phage, virus, prion, bacteria, DNA, RNA, gene. In some embodiments, the metal oxide in coating 130 is a transition metal oxide, titanium oxide, tantalum oxide, zirconium oxide, zinc oxide, niobium oxide. In other embodiments coating 130 consists of a metal oxide and a polymer or copolymer.

The polymer or copolymer used in one or all of the coating layers may be functionalized, such as a siloxane with methoxy and amine groups. In such a case, the functional groups may be used to tether or immobilize drugs, antibiotics, biologics, proteins, peptides, phages, and other molecules traditionally stabilized to surfaces using layer by layer self-assembly and silanization techniques. The advantage of type of the described wet chemistry, sol-gel type hybridization over the prior art is that the same coating can function as a non-resorbable bioactive surface, a diffusion barrier and a delivery matrix while having other active agents immobilized to the surface of the barrier layer. In other cases the polymer or copolymer can be based on polyurethanes.

Figure 3:
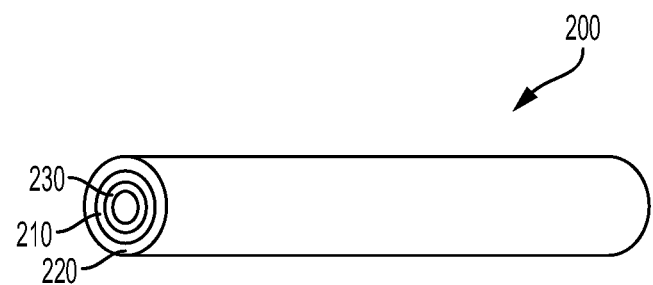
FIG. 3 is a cross-sectional perspective view of a coated catheter in accordance with the subject technology.

An example of a medical device having multiple coatings described above is a coated catheter. As shown in FIG. 3, a catheter 200 includes a catheter body 230, a coating reservoir 210 supported by the outer surface of catheter body 230, and a barrier coating 220 supported by the inner surface of reservoir coating 210. In some embodiments, both coatings 210, 220 can include a metal oxide (e.g., a titanium oxide) and a polymer. In some embodiments, coatings 210, 230 can have different compositions (e.g., different metal oxides and/or different polymers).

Figure 4:
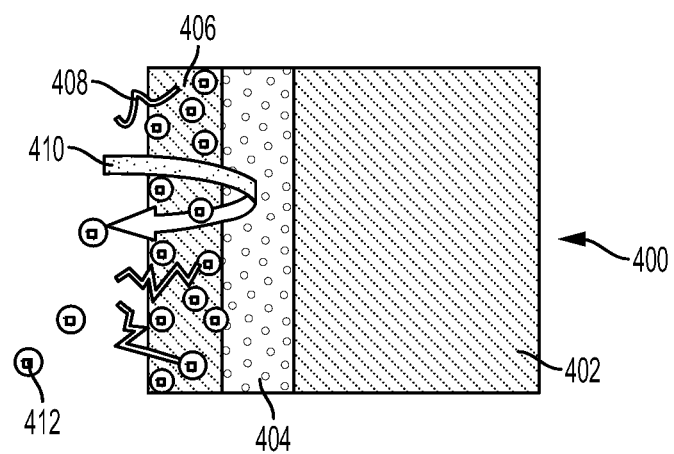
FIG. 4 illustrates a sustained release delivery system in accordance with the subject technology.
Figure 5:
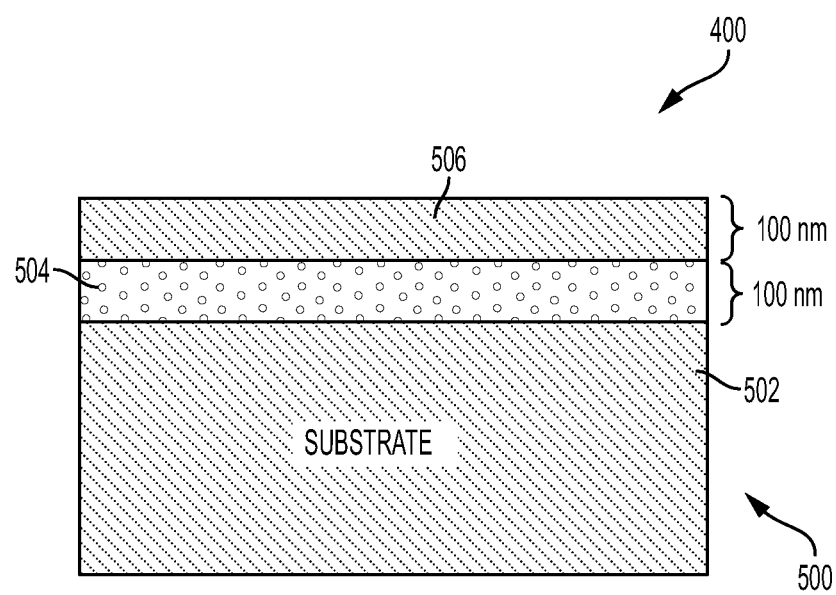
FIG. 5 illustrates a view of another sustained release delivery system in accordance with the subject technology.

A more detailed schematic of a delivery system 400 is shown in FIG. 4 and FIG. 5. The delivery system 400 shows a general and specific example of a reservoir and barrier system in FIGS. 4 and 5, respectively. The delivery system 400 may be applied to catheters, dental implants, provisional dental restorations, orthopedic trauma implants, nails, bone screws, bone plates, external fixation pins and wires, joint replacements, and wound dressings as well as urinary catheters, blood contacting catheters, endotracheal tubes and other airway management devices. The delivery system 400 may be applied to hospital furniture, disposable cloths and drapes, medical and surgical instruments and equipment to prevent bacteria growth and infection through sustained delivery of silver ions, copper ions, zinc, biologics or drugs. The system 400 may be applied directly to the skin or epithelial layers for transepithelial pharmacological delivery or applied to internal organs of the body for localized and systemic delivery of bioactive agents.

A composition used to form a metal oxide and polymer coating, methods of preparation and application are disclosed, which create a long lasting sunscreen. After application of the composition, the metal oxide precursor decomposes and polymerizes with the polymer precursor to form a coating of metal oxide and polymer which also binds to the surface of the skin, providing long lasting water resistance and protection from UVA and UVB. The metal oxide consists of a UV absorbing mineral such as titanium oxide, zinc oxide or a mixture of the two. The polymer consists of at least one functionalized polymer which binds to keratin and facilitates copolymerization of the metal oxide and polymer precursors. An example is provided in Example 8 below.

Example 8 included the use of the metal oxide and polymer forming solutions in conjunction with FDA recognized sunscreens, to form a sunscreen that is water resistant. The added ingredients include: Aminobenzoic acid (PABA) up to 15 percent; Avobenzone up to 3 percent; Cinoxate up to 3 percent; Dioxybenzone up to 3 percent; Homosalate up to 15 percent; Menthyl anthranilate up to 5 percent; Octocrylene up to 10 percent; Octyl methoxycinnamate up to 7.5 percent; Octyl salicylate up to 5 percent; Oxybenzone up to 6 percent; Padimate O up to 8 percent; Phenylbenzimidazole sulfonic acid up to 4 percent; Sulisobenzone up to 10 percent; Titanium dioxide up to 25 percent; Trolamine salicylate up to 12 percent; Zinc oxide up to 25 percent; Ensulizole up to 4 percent; Homosalate up to 15 percent; Meradimate up to 5 percent; Octinoxate up to 7.5 percent; Octisalate up to 5 percent; Octocrylene up to 10 percent; Oxybenzone up to 6 percent; and Padimate O up to 8 percent.

The subject technology also includes systems for delivery of the coatings to the point of use. The systems include dose applicator swabs and spray applicators. One form of this system is a single-use pop ampoule applicator, which contains one, two, three or more glass or plastic ampoules. The applicator system and contents are either sterile or non-sterile depending on the end use. The ampoules keep the metal oxide and polymer precursors from reacting and polymerizing before use. The ampoules also contain the solvents used to suspend the precursors, like alcohols, isopropoanol, ethanol, methanol, and hexanes, xylenes, terpenes, terpineol, lavender oil, (R)-(+)-LIMONENE, (S)-(–)-LIMONENE, ALPHA-TERPINENE, Orange Terpinene. Tandem pop ampoule dose applicator. Metal oxide and polymer precursors and active agents like silver compounds mixed with solvents such as isopropanol, hexanes in Ampoules. Crushing of the ampoules releases the contents and allows the Components to mix and flow out to the applicator tip. The coating is then brushed or dabbed onto the desired surface.

Referring in particular to FIG. 4, a sustained release hybrid delivery system 400 is shown in cross-section. The system 400 can be application to an item 402 such as a trauma nail, pin, screw, endoprosthesis, catheter and the like. The item 402 can be any kind of substrate such as Titanium, Cobalt-Chromium, stainless steel type 316, polymers and the like.

A reservoir layer 404 is applied to the substrate 402. The reservoir layer 404 can be concentrated bioactive and antimicrobial agents such as ion forming metals like Silver, Copper, Zinc, Vanadium. The reservoir layer 404 can also include drugs, bioactive molecules and/or reagents like iron compounds. A bioactive diffusion layer 406 is applied to the reservoir layer 404. The bioactive diffusion layer 406 can include immobilized drugs or crystalline titanium oxide 408. Preferably, water can diffuse into the coatings 408 as represented by arrow 410. When an item 402 is coated, sustained deliver out to adjacent tissues is accomplished as indicated by items 412. The items 412 may be metal ions like silver, copper, zinc and vanadium, drugs, bioactive molecules, and reaction agents like iron.

Referring again to FIG. 5, another cross-sectional view of a system 500 is shown. The system 500 has a similar structure to system 400 and thus similar portions are references as a "5" series number instead of a "4" series number. The reservoir layer 504 and the bioactive diffusion layer 506 can both be about 100 nm thick. In one example, the reservoir layer is $(Ag_2O)_y(TiO_2)(C_aH_bOSi)_z$. The bioactive diffusion layer 506 has a rate controlling coating of $(TiO_2)_x(Ag_2O)_y(TiO_2)(C_aH_bOSi)_z$.

Figure 6A:
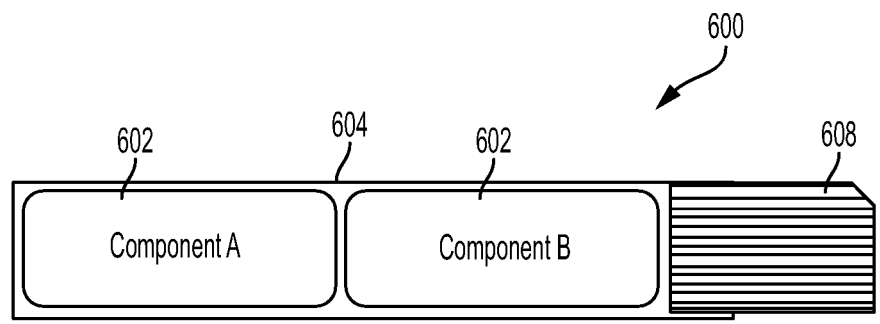
FIG. 6A is a tandem pop ampoule dose applicator in accordance with the subject disclosure.
Figure 6B:
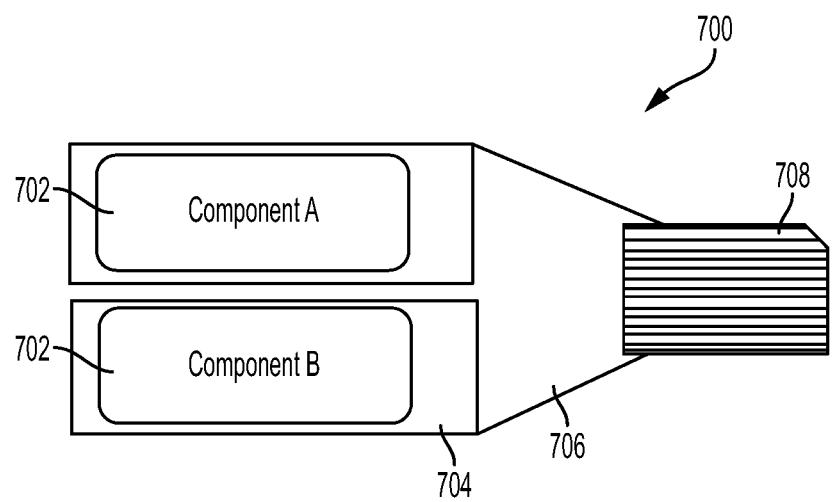
FIG. 6B is a parallel pop ampoule dose applicator in accordance with the subject disclosure.

Tandem (top) and parallel (bottom) pop ampoule, dose applicators 600, 700 are depicted in FIGS. 6A and 6B. As shown in FIG. 6A, ampoules 602 can be arranged in series with mixing taking place in a mixing tube 604. Alternatively as shown in FIG. 6B, ampoules 702 can be arranged in parallel with mixing taking place in a mixing chamber space 706 defined between the ampoules 702 and a brush tip 708 mounted on the mixing tube 704. Alternately, the tip 708 can be a sponge or other arrangement so that the mixing can take place within the sponge itself.

In one embodiment, metal oxide and polymer precursors and active agents like silver compounds mixed with solvents such as isopropanol, hexanes are placed together or separately in the ampoules. Crushing of the ampoules releases the contents and allows the components to mix and flow out to the applicator tip 608, 708. The coating is then brushed or dabbed onto the desired surface. In one example, component B contains titanium isopropoxide and meth-oxy functionalized polydimethylsiloxane at ratio of about 95:5, which is then diluted to about a 1.25% solution with isopropanol or a mixture of isopropanol and hexanes. Component A is a therapeutic ingredient that mixes with and is transported by component B, after the ampoules or chambers are opened.

Component A can be a silver compound mixed with solvents. Specifically, silver neodecanoate is used as a powder or preferably mixed with the solvent hexane or a mixture of hexane and xylene. A moderate dose of silver would consist of component B chemicals mixed together at room temperature and by volume in the ratios of 1:0.01:82.8:6.54:2.0 (respectively for titanium isopropoxide, methoxy amine functionalized polydimethylsiloxane, and isopropanol). Component A chemicals mixed together at room temperature and by volume in the ratios of 6.54:2.0 (respectively for hexanes and the dopant 25% silver neodecanoate in xylenes). Each component would be placed in a glass ampoule 602, 702 or a sealed chamber within the dose applicator 600, 700. The color of a coating formed by this chemistry is generally white, clear to dark brown on a man-made substrate, skin or similar tissues.

Another example containing more silicone would be component B chemicals mixed together at room temperature and by volume in the ratios of 1:0.1:82.8 (respectively for titanium isopropoxide, methoxy amine functionalized polydimethylsiloxane, and isopropanol). Component A chemicals mixed together at room temperature and by volume in the ratios of 6.54:2.0 (respectively for hexanes and the dopant 25% silver neodecanoate in xylenes). Each component would be placed in a glass ampoule or a sealed chamber within the applicator. The color of a coating formed by this chemistry is generally white, clear to dark brown on a man-made substrate, skin or similar tissues.

Typically, metal oxide and polymer precursors and active agents like silver compounds mixed with solvents such as isopropanol, hexanes in Ampoules. Crushing of the ampoules by squeezing or external pressure releases the contents and allows the Components to mix and flow out to the applicator tip. The coating is then brushed or dabbed onto the desired surface. In this example Component B contains titanium isopropoxide and meth-oxy functionalized polydimethylsiloxane at ratio of about 95:5, which is then diluted to about a 1.25% solution with isopropanol or a mixture of isopropanol and hexanes. Component A is a therapeutic ingredient that mixes with and is transported by Component B, after the ampoules or chambers opened. In this example Component A is a silver compound mixed with solvents. Specifically, silver neodecanoate is used as a powder or preferably mixed with the solvent hexane or a mixture of hexane and xylene.

Alternately, components A and B are dispensed with as an aerosol using pump action or propellant. A suitable double-chamber aerosol container for the packaging of products with several components which are to come into contact and be mixed at the time of use is described in U.S. Pat. No. 4,593,836 issued Jun. 10, 1986 to Lilienthal and U.S. Pat. No. 7,789,278 B2 issued Sep. 7, 2010 to Ruiz de Gopegui, each of which is incorporated herein by reference.

One of the advantages of the pop ampule dose applicators and the aerosols described is that the coatings can be mixed and applied in a portable fashion at the point of use. Sterile applicators and aerosols described above would be used in the medical setting or surgical field to create the coatings directly to the skin as a surgical preparation or sunblock, an antimicrobial barrier on body tissues, or onto medical devices, instruments, hospital fixtures or medical implants. Examples of medical devices include orthopedic implants, fracture fixation, devices, plates, screws, rods, the surface of artificial joints, dental implants, medical tubing, catheters, urinary catheters, and wound dressings. Multiple applicators or aerosols can be used to apply multiple coatings as depicted in FIG. 2 and described in detail above.

Example 1

Coatings are formed on an article, medical device or implant, such as a catheter, fracture fixation device, joint replacement, wound dressing or applied directly to a structure or tissues of the body, such as the skin, bone, muscle or organs from a composition consisting of a liquid precursor solution of titanium isopropoxide, methoxy amine functionalized polydimethylsiloxane, isopropanol and hexanes and the dopant silver neodecanoate. For the reservoir layer, these chemicals are mixed together at room temperature and by volume in the ratios of 1:0.01:10.35:0.817:2.0 (for titanium isopropoxide, methoxy amine functionalized polydimethylsiloxane, isopropanol and hexanes and the dopant silver neodecanoate respectively), while the outermost layer forming the diffusion barrier is mixed in the ratios of 1:0.1:10.35:0.817:0.2 (respectively). In this case, the reservoir layer is made from a solution containing ten times more silver than the barrier layer. The reservoir chemistry also contains ten times more PDMS, to aid in the release of the silver ions. The barrier layer has a lower concentration of PDMS to improve mammalian cellular adhesion in this instance. The reservoir layer is sprayed onto the substrate using the chemistry described for this layer using a gravity fed sprayer with an air pressure of 40 psi to deposit the solvents and precursors uniformly onto the cleaned surface of the medical device substrate. The solvent is allowed to flash in at room temperature and under atmospheric conditions, leaving a yellow to white coating of approximately 100-500 nm in thickness. Thinner coatings may alternately be applied to create a spectrum of interference colored appearance from red to purple and blue. A single or multiple layers of the reservoir composition may be applied by the same technique until the desired volume of dopants is applied to the device. A slightly elevated temperature of approximately 37 C to 41 C or 80 C could be used to speed flashing and evaporation of the solvents. This elevated temperature may be applied by resistance heating, convection, infrared or ultraviolet lighting systems. A final layer of coating is then applied to form the diffusion barrier layer using the second chemical composition and a similar spraying technique and allowed to air-dry, forming a final layer of approximately 100-500 nm in thickness. Alternately, the coatings can be applied using electrostatic spraying techniques, airless spraying or sprayed using inert or active gases or hydrocarbons as the propellant in place of air.

Example 2

A dip coating method may be used to apply the coating system. In this case, the volume of the solvents would be increased by approximately eight fold to facilitate the formation of a unified coating. For this method, the reservoir layer chemicals would be mixed together at room temperature and by volume in the ratios of 1:0.01:82.8:6.54:2.0 (respectively for titanium isopropoxide, methoxy amine functionalized polydimethylsiloxane, isopropanol and hexanes and the dopant silver neodecanoate), while the outermost layer forming the diffusion barrier is mixed in the ratios of 1:0.1:82.8:6.54:0.2 (respectively). The medical device would then be dipped into the reservoir solution at a rate of approximately 4 inches per second and withdrawn at a rate of approximately 2 inches per second, under normal atmospheric conditions and room temperature. A slightly elevated temperature of approximately 37 C to 41 C or 80 C can be used to speed flashing and evaporation of the solvents. This elevated temperature may be applied by resistance heating, convection, infrared or ultraviolet lighting systems. The resulting being a yellow to white coating of approximately 100-500 nm in thickness. The dipping may be repeated to achieve the desired thickness and loading of active agents. A final layer of dip coating is then applied to form the diffusion barrier layer using the second chemical composition and a similar dipping technique and allowed to air-dry with or without the addition of heat and photon energy, forming a final yellow to white layer of approximately 100-500 nm in thickness. Thinner coatings may alternately be applied to create a spectrum of interference colored appearance from red to purple and blue. The color of the final coating is directly related to the thickness of the coatings as is achieved with anodization of titanium alloys. The invention includes the use of these chemistries and methods to create these colors on devices.

Example 3

Solutions formed from solid state suspensions for metal oxides and polymers can be used to create coatings with broad spectrum photoactivity as described in the patent applications: U.S. PGPUB No. 2009/0104095, U.S. Ser. No. 12/253,530 to Jarrell et al. filed Oct. 17, 2008 entitled Method of Making a Composite from Metal Oxide and Polymer Precursors; U.S. PGPUB No. 2009/0105384, U.S. Ser. No. 12/253,555); U.S. PGPUB No. 2009/0104473, U.S. Ser. No. 12/253,354 filed Oct. 17, 2008 entitled Novel Compositions and Related Methods, Coatings, and Articles; and U.S. PGPUB No. 2011/0092870, U.S. Ser. No. 12/975, 218 filed Dec. 21, 2010 entitled Composition including metal oxide and polymer. This photoactivity is related to the formation of valence electrons in the presence of photons from x-rays to infrared which also produces superoxide in the presence of moisture or water.

The reaction does not yield a large amount of hydroxyl radials when compared to the photocatalytic properties of crystalline titanium oxide exposed to ultraviolet radiation. The addition or formation of iron particles within the coating promotes increased hydroxyl radical production from superoxide using the Fenton reaction. This could be added in the form of iron oxide nano particles or by use of iron (II) sulfate or similar iron source for the Fenton reaction. The production of the hydroxyl radical by this reaction is effective for decontamination of surrounding area and destruction of microbes such as bacteria, viruses and fungi on medical devices, until the iron eluted from the coating and during irradiation by a broad spectrum of radiation, such as medical x-rays or phototherapy using ultraviolet, visible and infrared wavelengths. Coating systems and irradiation schemes, as disclosed herein, may also be used to create general purpose filters and purification systems to destroy organic compounds and microbes in air and liquid purification systems.

For the reservoir layer, these chemicals are mixed together at room temperature and by volume in the ratios of 1:0.01:10.35:0.817:2.0 (for titanium isopropoxide to methoxy amine functionalized polydimethylsiloxane to isopropanol to hexanes to the dopant silver neodecanoate respectively), while the outermost layer forming the diffusion barrier is mixed in the ratios of 1:0.02:10.35:0.817:0.2: 0.1 (for titanium isopropoxide to methoxy amine functionalized polydimethylsiloxane to isopropanol to hexanes to the dopant silver neodecanoate and a 20% solution (wt/vol) in isopropanol of ferric nitrate nonahydrate or ferric chloride hexahydrate or ferric chloride salt [iron compounds per Gash, et. al., Chem. Mater. 2001, 13, 999-1007] or nano (~10 nm) iron oxide (II, III) particulate respectively). These two types of layers are applied by spray coating as described in Example 1 or diluted with eight times more solvent and dip coated according to Example 2. These two coating may be applied to the inside of a 20 ml glass scintillation vessel to create a photocatalytic reaction chamber for producing hydroxyl and superoxide in the presence of broad spectrum photon irradiation from x-rays to infrared.

Example 4

Alternately water, acids or bases may be mixed with the coating solutions to form sols and particulate forms within the solvent carriers. Ceramics, plastics, metals, oxides or salts may be mixed in the coating solutions to influence the bioactivity mechanical, physical properties or controlled delivery properties of the coatings. Crystalline titanium oxide particles within sols or nano particles (i.e. AEROX-IDE® TiO2 P 25 available from the Evonik Degussa Corporation) may be mixed in with the solutions to impart photocatalytic properties to the coatings under ultraviolet radiation. This can be used to enhance the generation of electron and hole pairs in the presence of photons, which produce reactive oxygen species namely the hydroxyl radical and superoxide in the presence of moisture or water. This enables the conversion of the non-discrete valance electrons and holes created during photon irradiation of the amorphous titanium oxide and polymer composition coatings into discrete electrons and holes associated with crystalline titanium oxide and the photocatalytic process produced by the crystalline semi-conductor material. This allows delivery of discrete electrical charges from broad spectrum photon irradiation, thus extending the phenomena seen with the dye-sensitized titanium oxide solar cell, below the ultraviolet range into x-rays and above the visible range into the infrared spectrum. Extending the spectral response is an advantage over the prior art. U.S. Pat. No. 5,084,365 to Gratzel, et. al., entitled Photo-electrochemical cell and process of making same, provides background information.

For the reservoir layer, these chemicals are mixed together at room temperature and by volume in the ratios of 1:0.01:10.35:0.817:2.0 (for titanium isopropoxide to methoxy amine functionalized polydimethylsiloxane to isopropanol to hexanes to the dopant silver neodecanoate respectively), while the outermost layer forming the diffusion barrier is mixed in the ratios of 1:0.02:10.35:0.817:1 (for titanium isopropoxide to methoxy amine functionalized polydimethylsiloxane to isopropanol to hexanes to 20% Degusa P25 nano crystalline titanium oxide solution in isopropanol (wt to volume)). These two types of layers are applied by spray coating as described in Example 1 or diluted with eight times more solvent and dip coated according to Example 2. These two coating may be applied to the inside of a 20 ml glass scintillation vessel to create a photocatalytic reaction chamber for producing hydroxyl and superoxide in the presence of broad spectrum photon irradiation from x-rays to infrared.

Example 5

A drug may be incorporated into the outer barrier layer for elution and or immobilization. For the reservoir layer, these chemicals are mixed together at room temperature and by volume in the ratios of 1:10 (25% silver neodecanoate in xylenes to isopropanol respectively), while the outermost layer forming the diffusion barrier is mixed in the ratios of 1:0.03:10.35:0.817:0.002:1 (for titanium isopropoxide to methoxy amine functionalized polydimethylsiloxane to isopropanol to hexanes to 25% silver neodecanoate in xylenes to 10% solution/slurry of Lortadine or diphenhydramine in ethanol or isopropanol (wt/vol)). These two types of layers are applied by spray coating as described in Example 1 or diluted with eight times more solvent and dip coated according to Example 2.

Example 6

Drugs may be dissolved within the carrier for the coating system or dissolved within the metal oxide precursor and or polymer precursor. Ibuprofen is an example of a drug which is soluble within the alcohol-based carrier system used for applying the coatings. In this case, 0.2 grams of ibuprofen are dissolved in 1 ml of isopropanol to create a saturated or near saturated solution. The isopropanol with dissolved drug is them used in place of isopropanol to create one or more of the layers described in Examples 1-5. The anti-inflammatory drugs phenylbutazone and nabumetone, may be dissolved into the polydimethylsiloxane at a concentration of 80 mg/L and the polydimethylsiloxane with dissolved drug used to replace the polydimethylsiloxane described in Examples 1-5. The 25% silver neodecanoate in xylenes may be mixed with drugs soluble in decanoaic acid, such as nandrolone, fluphenazine, bromperidol, haloperidol and vanoxerine and the silver necodecanoate with dissolved drug use to replace the silver neodecanoate in 25% xylenes described in Examples 1-5.

Example 7

One or both layers of the delivery system are applied using a pen-type applicator, directly to the substrate which may be skin other tissues or medical devices. The pen consists of a barrel with one or more compartments for holding the procurer solutions separate until the time of application and an absorbent tip for dispensing a thin film of the precursor solutions.

Example 8

The use of the solutions in conjunction with FDA recognized sunscreens can form a sunscreen that is water resistant. The added ingredients include: Aminobenzoic acid (PABA) up to 15 percent; Avobenzone up to 3 percent; Cinoxate up to 3 percent; Dioxybenzone up to 3 percent; Homosalate up to 15 percent; Menthyl anthranilate up to 5 percent; Octocrylene up to 10 percent; Octyl methoxycinnamate up to 7.5 percent; Octyl salicylate up to 5 percent; Oxybenzone up to 6 percent; Padimate O up to 8 percent; Phenylbenzimidazole sulfonic acid up to 4 percent; Sulisobenzone up to 10 percent; Titanium dioxide up to 25 percent; Trolamine salicylate up to 12 percent; Zinc oxide up to 25 percent; Ensulizole up to 4 percent; Homosalate up to 15 percent; Meradimate up to 5 percent; Octinoxate up to 7.5 percent; Octisalate up to 5 percent; Octocrylene up to 10 percent; Oxybenzone up to 6 percent; and/or Padimate O up to 8 percent.

Example 9

A tandem pop ampoule, dose applicator is depicted in FIG. 6A is used. Metal oxide and polymer precursors and active agents like silver compounds mixed with solvents such as isopropanol, hexanes are placed together or separately in Ampoules. Crushing of the ampoules releases the contents and allows the Components to mix and flow out to the applicator tip. The coating is then brushed or dabbed onto the desired surface. In this example, component B contains titanium isopropoxide and meth-oxy functionalized polydimethylsiloxane at ratio of about 95:5, which is then diluted to about a 1.25% solution with isopropanol or a mixture of isopropanol and hexanes. Component A is a therapeutic ingredient that mixes with and is transported by component B, after the ampoules or chambers opened. In this example, component A is a silver compound mixed with solvents. Specifically, silver neodecanoate is used as a powder or preferably mixed with the solvent hexane or a mixture of hexane and xylene.

A moderate dose of silver would consist of Component B chemicals mixed together at room temperature and by volume in the ratios of 1:0.01:82.8:6.54:2.0 (respectively for titanium isopropoxide, methoxy amine functionalized polydimethylsiloxane, and isopropanol). Component A chemicals mixed together at room temperature and by volume in the ratios of 6.54:2.0 (respectively for hexanes and the dopant 25% silver neodecanoate in xylenes). Each component would be placed in a glass ampoule or a sealed chamber within the dose applicator. The color of a coating formed by this chemistry is generally white, clear to dark brown on a man-made substrate, skin or similar tissues.

Another example containing more silicone would be component B chemicals mixed together at room temperature and by volume in the ratios of 1:0.1:82.8 (respectively for titanium isopropoxide, methoxy amine functionalized polydimethylsiloxane, and isopropanol). Component A chemicals mixed together at room temperature and by volume in the ratios of 6.54:2.0 (respectively for hexanes and the dopant 25% silver neodecanoate in xylenes). Each component would be placed in a glass ampoule or a sealed chamber within the applicator. The color of a coating formed by this chemistry is generally white, clear to dark brown on a man-made substrate, skin or similar tissues.

It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements shown as distinct for purposes of illustration may be incorporated within other functional elements in a particular implementation. All patents, patent applications and other references disclosed herein are hereby expressly incorporated in their entireties by reference. While the subject technology has been described with respect to preferred embodiments, those skilled in the art will readily appreciate that various changes and/or modifications can be made to the subject technology without departing from the spirit or scope of the invention as defined by the appended claims.

What is claimed is:

1. An applicator for coating an article comprising:
a first container having a reservoir coating material to be supported directly on a surface of the article, the reservoir coating including a polymer;
a second container having a diffusion barrier coating material to be applied on top of the reservoir coating material, the reservoir coating material containing a higher concentration of active ingredients and the diffusion barrier coating material containing a lower concentration of active ingredients to enable the diffusion barrier coating material to act as a rate controlling diffusion barrier;
a mixing tube, the first and second containers housed within the mixing tube; and
an applicator tip, the applicator tip attached to the mixing tube.

2. An applicator as recited in claim 1, wherein the diffusion barrier coating material becomes a dried diffusion barrier including a metal oxide after application.

3. An applicator as recited in claim 2, wherein the metal oxide is a transition metal oxide and the polymer is functionalized.

4. An applicator as recited in claim 1, wherein the reservoir coating material includes at least one active ingredient for delivery, the first container includes a solvent, and the second container contains a liquid.

5. An applicator as recited in claim 2, wherein the metal oxide is selected from the group consisting of titanium oxides, vanadium oxides, zinc oxides, zirconium oxides, silver oxides, tantalum oxides, or combinations thereof.

6. An applicator as recited in claim 1, wherein each of the first and second containers are ampoules.

7. An applicator as recited in claim 1, wherein the article is human skin for transepithelial pharmacological delivery for delivery of a bioactive agent in the reservoir coating material.

8. An applicator as recited in claim 1, wherein the second container includes an additive selected from the group consisting of:
Aminobenzoic acid (PABA) up to 15 percent;
Avobenzone up to 3 percent;
Cinoxate up to 3 percent;
Dioxybenzone up to 3 percent;
Homosalate up to 15 percent;
Menthyl anthranilate up to 5 percent;
Octocrylene up to 10 percent;
Octyl methoxycinnamate up to 7.5 percent;
Octyl salicylate up to 5 percent;
Oxybenzone up to 6 percent;
Phenylbenzimidazole sulfonic acid up to 4 percent;
Sulisobenzone up to 10 percent;
Titanium dioxide up to 25 percent;
Trolamine salicylate up to 12 percent;
Zinc oxide up to 25 percent;
Ensulizole up to 4 percent;
Meradimate up to 5 percent;
Octinoxate up to 7.5 percent;
Octisalate up to 5 percent;
and
Padimate 0 up to 8 percent.

9. An applicator as recited in claim 1, wherein the second container contains 95% titanium isopropoxide and 5% methoxy functionalized polydimethylsiloxane, which is diluted to about a 1.25% solution with isopropanol or a mixture of isopropanol and hexanes.

10. An applicator for coating for an article comprising:
a first ampoule having a reservoir coating to be supported directly on a surface of the article, the reservoir coating including a polymer;
a second ampoule having a diffusion barrier coating to be applied on top of the reservoir coating, the diffusion barrier coating including a metal oxide, the reservoir coating containing a higher concentration of active ingredients and the diffusion barrier coating containing a lower concentration of active ingredients to enable the diffusion barrier coating to act as a rate controlling diffusion barrier;
a mixing tube, the first and second ampoules housed within the mixing tube; and
an applicator tip, the applicator tip attached to the mixing tube.

11. An applicator as recited in claim 10, wherein the first ampoule includes a solvent.

12. An applicator as recited in claim 10, wherein the reservoir coating including at least one active ingredient for delivery.

13. An applicator as recited in claim 10, wherein the first and second ampoules are in a form of first and second distinct containers.

14. An applicator as recited in claim 13, wherein the first and second distinct containers are first and second tubes.

* * * * *